United States Patent [19]

Uede et al.

[11] Patent Number: 4,753,757

[45] Date of Patent: Jun. 28, 1988

[54] PROCESS FOR PREPARING SOLID ACETYL PHOSPHATE SALT

[75] Inventors: Yoichiro Uede; Teruo Otomo, both of Himeji, Japan

[73] Assignee: Daicel Chemical Industries, Inc., Sakai, Japan

[21] Appl. No.: 693,657

[22] Filed: Jan. 22, 1985

[30] Foreign Application Priority Data

Feb. 13, 1984 [JP] Japan ................................ 59-22852
May 25, 1984 [JP] Japan ............................. 59-105914

[51] Int. Cl.$^4$ ............................................. C07F 5/02
[52] U.S. Cl. .................................................. 260/545 P
[58] Field of Search ..................................... 260/545 P

[56] References Cited

FOREIGN PATENT DOCUMENTS 2831831 2/1980 Fed. Rep. of Germany .
144546 6/1979 German Democratic Rep. .

OTHER PUBLICATIONS

Avison, A. W. D., J. Chem. Soc., vol. 732, (1955), pp. 732–738.
Stadtman, E. R. et al., J. Biol. Chem., vol. 185, (1950), pp. 549–551.
Lewis, Jerome M., J. Org. Chem., vol. 44, (1979), pp. 364–365.

Primary Examiner—Paul J. Killos
Attorney, Agent, or Firm—Flynn, Thiel, Boutell & Tanis

[57] ABSTRACT

A salt of monoacetyl phosphate which is useful in the field of enzymatic reactions can be obtained as a precipitate by using a specified amount of lithium ion as a precipitating agent in the process for the acetylation of phosphoric acid or its salt with acetic anhydride. The resulting precipitate can be separated from the reaction mixture by filtration without necessity of operation at a low temperature or the replacement of solvents.

13 Claims, No Drawings

PROCESS FOR PREPARING SOLID ACETYL PHOSPHATE SALT

FIELD OF THE INVENTION

The present invention relates to a process for the preparation of a solid lithium salt of acetyl phosphate, more particularly, monoacetyl phosphate, by the use of orthophosphoric acid (hereinafter referred to also as phosphoric acid) or its salt as a raw material.

Certain salts of monoacetyl phosphate, for example, dilithium salt, diammonium salt, disodium salt or lithium potassium salt, are known to serve as a substrate of acetate kinase and therefore can be used in enzymatic reactions in which adenosine triphosphate (ATP) takes part. The present invention relates to a process for the preparation of the salts of monoacetyl phosphate that can be used in such a field.

Up to this time, salts of acetyl phosphate to be used in enzymatic reactions have been prepared by comparatively complicated processes. According to the present invention, the product salts of a high purity can be obtained by a process which comprises merely reacting phosphoric acid or its salt with acetic anhydride as an acetylating agent and lithium ion as a precipitating agent without complicated separation sequences required in the prior art.

BACKGROUND OF THE INVENTION

It is known that the acetylation of phosphoric acid by the use of an acetylating agent such as acetic anhydride or ketene can give mixtures of monoacetyl phosphate and diacetyl phosphate, occasionally further containing triacetyl phosphate. A crystalline salt of monoacetyl phosphate to be used in the above enzymatic reaction can be separated from these mixtures. Representative methods include a process for the preparation of diammonium acetyl phosphate which comprises acetylating 100% phosphoric acid with acetic anhydride in ethyl acetate and pouring the reaction mixture into chilled methanol saturated with ammonia (G. M. Whitesides et al., J. Org. Chem. 44, 864). However, this method involves an operation at low temperatures, i.e. $-30$ TO $-10°$ C., and the formed diammonium acetyl phosphate tends to decompose in the presence of excess ammonia, so that the reaction conditions must be strictly controlled in order to carry out the separation by filtration smoothly. Alternatively, salts of acetyl phosphate can be obtained in the form of an aqueous solution from the above acetylation reaction mixture (D. C. Crans and G. M. Whitesides, J. Org. Chem. 48, 3130–32), but the product is inconvenient for the storage or the use as compared with the solid one, because acetyl phosphate hydrolyses in an aqueous solution.

It is also known that a salt of phosphoric acid is acetylated with acetic anhydride to obtain a salt of acetyl phosphate, as described in West German Patent No. 2831831 or East German Pat. No. 144546. In these patents, acetic anhydride or its mixture with acetic acid was used as a medium, and the examples disclosed in these patents demonstrated that when the acetylation of sodium or potassium phosphate was carried out in acetic anhydride or its mixture with acetic acid in which sodium or potassium phosphate can not be dissolved, the reaction proceeded to the stage of diacetyl phosphate. Accordingly, as described in the latter half of the East German Patent, solvolysis with alcohol etc. was necessary to obtain monoacetyl phosphate from the diacetyl derivative. Up to this time, the acetylation of lithium phosphate was disclosed only in the West German Patent No. 2831831. According to Example 1 of this patent, a solution of lithium hydroxide (12 parts or 0.5 molar part) in acetic anhydride (408 parts or 4 molar parts) is added dropwise to a mixture of 100% phosphoric acid (49 parts or 0.5 molar part) and acetic anhydride (204 parts or 2 molar parts) in a nitrogen atmosphere under stirring, and the resulting mixture is further stirred at 40° to 50° C. for 2 hours to obtain a pale yellow, transparent reaction mixture. This mixture is evaporated to dryness under a reduced pressure at 65° C. by the use of a rotary evaporator to obtain a white solid residue (93 parts). All analyses such as elemental analysis, ignition test, acetyl group determination or titration with potassium hydroxide ensure that this residue is lithium diacetylphosphate.

As described above, the acetylation of lithium phosphate with acetic anhydride according to the prior art proceeds easily to the diacetyl product stage, and gives a homogeneous solution.

Lithium monoacetyl phosphate itself, which is selected as a salt suitable for obtaining acetyl phosphate in the form of a solid salt in the present invention, is already well known in the purification and isolation of monoacetyl phosphate from an aqueous solution (see E. R. Stadtman and F. Lipmann, J. Biol. Chem., 185, 549–551; Methods in Enzymology, vol. III, pp. 228–231, ed. S. P. Colowick and N. 0. Kaplan (1957); D. E. Koshland, Jr., J. Amer. Chem. Soc., 73, 4103; A. W. D. Avison, J. Chem. Soc., 1955, 736). These separation methods are based on the property of dilithium monoacetylphosphate that it is hardly soluble in a mixture of ethanol and water.

According to R. W. Porter et al. (J. Biol. Chem., 244, 1847) dilithium acetyl phosphate was precipitated by addition of methanol containing lithium acetate to an oily, evaporation residue which was obtained by treating monotriethylammonium salt of phosphoric acid, $(C_2H_5)_3NH\ H_2PO_4$, with acetic anhydride in acetonitrile for one hour at room temperature followed by removing volatile materials using a rotary evaporator.

As described above, the medium which has been used in the prior art to precipitate a lithium salt of acetyl phosphate is an alcoholic solvent which is reactive to acetic anhydride. Accordingly, the precipitation of the lithium salt could not be directly combined with the acetylation using acetic anhydride.

As described above, there is not known as yet a simple process for precipitating a crystalline salt of monoacetyl phosphate which can be easily handled from the acetylation product of phosphoric acid without recourse to a low temperature operation. Further, the acetylation of phosphate salts proceeds without control to the diacetyl product stage, and otherwise in order to precipitate a lithium salt of monoacetyl phosphate the replacement of the medium of acetylation by another medium was necessary.

SUMMARY OF THE INVENTION

The present invention enables one to overcome these shortcomings of the prior art and provides a new, simplified process for the preparation of a salt of monoacetyl phosphate by combining the acetylation step directly with the separation by precipitation.

The present invention relates to a process for the preparation of a salt of acetyl phosphate by acetylating a substrate selected from among phosphoric acid and its salts with acetic anhydride, wherein from 1.5 to 2.3 times by mole as much lithium ion as the substrate is present together with the acetylated substrate and a solid salt of monoacetyl phosphate is separated from the reaction mixture. In the present invention, "molar ratio" refers to not only molecules but also atoms, atomic groups and ions.

DETAILED DESCRIPTION OF THE INVENTION

The process of the present invention can be carried out typically according to the following three methods.

(1) A process which comprises treating the reaction mixture obtained by acetylating phosphoric acid with acetic anhydride in an inert solvent, with the amount of lithium ion 1.5 to 2.3 molar equivalent to phosphate radical to thereby precipitate acetyl phosphoric acid as a solid lithium salt.

(2) A process which comprises reacting a lithium salt of phosphoric acid having a molar ratio of lithium ion to phosphate radical of 1.5 to 2.2 with acetic anhydride in a solid-liquid coexistent state and separating a solid lithium salt of monoacetyl phosphate from the reaction mixture.

(3) A process which comprises acetylating sodium or potassium phosphate with acetic anhydride in acetic acid, adding an ionic lithium compound to the resulting reaction solution of the monoacetylation step to thereby precipitate monoacetyl phosphate in the form of its salt containing lithium and separating the precipitate from the reaction medium.

[Phosphoric acid process]

The first method, which is one of the representative methods for carrying out the process of the present invention, will be illustrated by the use of acetic acid as an inert solvent.

According to this method, orthophosphoric acid is acetylated by the use of a mixture of acetic acid and acetic anhydride and about 2 mol of lithium ion per mol of the orthophosphoric acid is added to the reaction mixture to thereby stop the reaction. Then, the reaction mixture is stirred to precipitate a lithium salt of monoacetyl phosphate, followed by separating the salt from the mother liquor. This method can be carried out in the same manner in an inert solvent other than acetic acid.

It has been found that a lithium salt of acetyl phosphate can be precipitated at an ordinary temperature in the form of solid which can be easily separated from the mother liquor containing an inert solvent by restricting the molar ratio of Li to $PO_4$ to about 2 (1.5 to 2.3). On the basis of this finding, the acetylation step has been combined directly with the separation by precipitation, thus simplifying the process.

This method needs neither the replacement of a solvent for the acetylation with an alcohol for the precipitation of the lithium salt as different from the prior art, nor a low temperature which has been needed in the ammonium salt precipitation method. According to the present invention, a salt of acetyl phosphate suitable as the substrate of acetate kinase can be easily obtained by the use of easily available starting materials and by operating at appropriately ordinary temperature.

The orthophosphoric acid to be used in this method may be hydrous or anhydrous. For example, 100% phosphoric acid (prepared by the method described, e.g., in J. Org. Chem., 40, 2518), 98% phosphoric acid (crystalline), 89% phosphoric acid, 85% phosphoric acid or 75% phosphoric acid can be used.

The acetylation of orthophosphoric acid is carried out in an inert solvent. The inert solvent must be one in which a mixture of acetic anhydride and phosphoric acid can be dissolved and which does not participate in an irreversible reaction with the mixture. Representative examples of the solvents to be used include acetates such as ethyl acetate, methyl acetate, isopropyl acetate or 2-ethoxyethyl acetate and ethers such as ethyl ether, isopropyl ether, tetrahydrofuran, dioxane and methyl tbutyl ether as well as acetic acid described above.

The molar ratio of an inert solvent to phosphoric acid at the beginning of the acetylation is preferably 2 to 15, still preferably 3 to 13.

The inert solvent is effective not only in decreasing the concentration of phosphoric acid and acetic anhydride in the acetylation to thereby allow the acetylation to proceed moderately, but also in ensuring a good mixing state through both steps of the acetylation and the precipitation. If no inert solvent is used, the condensation of phosphoric acid will accompany as a serious side reaction. If the acetylation is carried out at a low temperature, for example, from $-5°$ to $+5°$ C. to prevent the side reaction, the solvent-less acetylation system will become so viscous that the stirring of the system and the control of the reaction temperature will be difficult.

Acetic anhydride not only acts as an acetylating agent and a medium, but also reacts with water contained in the reaction mixture to form acetic acid, thus keeping the reaction system essentially water-free. The amount of acetic anhydride to be used is determined by considering the molar ratio of the water to the $PO_4$ group in the starting phosphoric acid. If the value obtained by subtracting the molar ratio of water to $PO_4$ from that of acetic anhydride to $PO_4$ is defined as the effective molar ratio of acetic anhydride, the amount of acetic anhydride to be used is generally determined in such a range as to give the effective molar ratio of at least 1.0. In the present invention, the effective molar ratio of acetic anhydride is preferably from 1.5 to 10, still preferably from 2.0 to 8.0.

If necessary, additional acetic anhydride may be added after the addition of ionic lithium compounds.

The acetylation temperature must be properly controlled to prevent rapid evolution of the reaction heat and to minimize side reactions such as the condensation of phosphoric acid. Further, the reaction temperature must be determined in such a range as to give a viscosity of the reaction mixture suitable for stirring and mixing. The preferred reaction temperature is varied depending on the kind and the amount of an inert solvent, but is generally 30° C. or below, at which the side reaction and the heat generation peak are not prominent. When acetic acid is used as an inert solvent, it is generally from 10 to 30° C.

The reaction time can be determined experimentally with the guidance of the results (yield and purity) obtained by carrying out the experiment at varied temperatures. When acetic acid is used as an inert solvent, it is generally from 30 minutes to 2 hours, preferably from 30 minutes to one hour.

After or during the acetylation, precipitation is carried out by the addition of lithium ion.

Preferred examples of the ionic lithium compounds which can provide lithium ion include lithium acetate (anhydrous), lithium acetate (dihydrate), lithium hydroxide (anhydrous), lithium hydroxide (monohydrate) and lithium carbonate. These compounds may be added in the form of powder or dispersion in acetic anhydride or an inert solvent such as acetic acid. After the addition, the reaction mixture is stirred until a homogeneous slurry is formed. The amount of the ionic lithium compound to be used is determined in such a range as to give a molar ratio of lithium ion to orthophosphoric acid of from 1.5 to 2.3, preferably from 1.8 to 2.3 and most preferably from 1.9 to 2.2. The addition is generally carried out at 30° C. or below, preferably at 20° C. or below.

A lithium salt of acetyl phosphate is formed as a white crystalline solid and it can be easily isolated from the reaction mixture by a solid-liquid separating method such as filtration. The product is washed with an organic solvent such as acetic acid and methanol and dried under a reduced pressure to give a powder. It is confirmed by analyses such as the enzymatic assay (see G. M. Whitesides et al, J. Org. Chem., 40, 2516–9), or liquid chromatography (Referential Example) that this powder is a lithium salt of monoacetyl phosphate containing 4.8 to 5.8 mmol/g of active phosphoric acid.

According to this method, lithium ion is added to the reaction mixture obtained by acetylating phosphoric acid with acetic anhydride in an inert solvent such as acetic acid, with a molar ratio of Li to PO$_4$ of near 2, to thereby obtain a crystalline salt of acetyl phosphate. This salt has a high purity (by the enzymatic assay) and can be easily handled and separated by the separation step directly combined with the acetylation step.

[Lithium phosphate process]

In the second method, a lithium salt of phosphoric acid is used as a raw material. This salt acts as a substrate for acetylation and provides at the same time lithium ion which is needed to precipitate the objective product.

Among lithium salts of phosphoric acid, only Li$_3$PO$_4$ is ordinarily available as a reagent, but the lithium salt of phosphoric acid to be used in the present invention need not be commercial products which are isolated and have a definite stoichiometric composition. That is to say, the useful lithium salts also include the mixtures prepared by mixing phosphoric acid with lithium ion sources. The mixtures, for example, are obtainable by adding an ionic lithium compound, namely, lithium acetate (anhydrous), lithium acetate (dihydrate), lithium hydroxide (anhydrous), lithium hydroxide (monohydrate), or lithium carbonate, to a homogeneous acetic acid solution of an available form of phosphoric acid, such as 100% phosphoric acid, 98% phosphoric acid (crystalline), 89% phosphoric acid, 85% phosphoric acid or 75% phosphoric acid, and stirring the resultant mixture until a homogeneous slurry is formed. Hereinafter, this slurry mixture is treated as lithium salts of phosphoric acid formally represented by the following formula (I) in a medium such as acetic acid.

$$Li_mH_nPO_4 \cdot xH_2O \qquad (I)$$

wherein m, n and x are each a positive number, and $m+n=3$, $m>0$, $x\geq 0$

The formula (I) shows only the composition of the above mixture as the molar ratio based on PO$_4$ radical, and does not always correspond to the actual state of a salt of phosphoric acid in the reaction mixture. "x" means the total amount of water both contained in starting materials and formed by the neutralization which may occur depending on the combination of the raw materials.

This method is characterized by using the raw materials having the specified molar ratio of lithium to phosphate radical. The lithium salts of phosphoric acid to be used are compounds represented by the formula (I) wherein preferably $2.2 \geq m \geq 1.5$, accordingly $1.5 \geq n \geq 0.8$ and, with respect to water, $6.0 \geq x \geq 0$, still preferably $2.1 \geq m \geq 1.9$ $1.1 \geq m \geq 0.9$ That is to say, when a salt substantially comprising dilithium phosphate is used, a lithium salt of monoacetyl phosphate can be obtained in a high yield. If m is outside the above stated range, the yield and the purity of the objective product will drop sharply.

In this method, acetic anhydride acts as an acetylating agent for the lithium salt of phosphoric acid, and the acetylation is generally carried out in the presence of acetic acid medium, that is to say, in a mixture of acetic acid and acetic anhydride. Acetic anhydride not only acts as an acetylating agent and a medium, but also reacts with water contained in the reaction mixture to form acetic acid, thus keeping the reaction system essentially water-free. The amount of acetic anhydride to be used is determined by considering the molar ratio of the water to the PO$_4$ group (i.e. x in the formula (I)) in the starting phosphoric acid. Here, if the value obtained by subtracting x from the molar ratio of acetic anhydride to a salt of phosphoric acid is defined as the effective molar ratio of acetic anhydride, the amount of acetic anhydride to be used is generally determined in such a range as to give the effective molar ratio of at least 1.0. In the present invention, the effective molar ratio of acetic anhydride is preferably from 1.5 to 10, still preferably from 2.0 to 8.0. Acetic acid is used in an amount enough to form a slurry in the preparation of a mixture of a salt of phosphoric acid, that is to say, in an amount enough to allow the reaction system to be stirred smoothly. Generally, the molar ratio of acetic acid to the salt of phosphoric acid at the beginning of the acetylation is preferably from 2 to 15, still preferably from 3 to 13.

With respect to the acetylation conditions, the temperature and the reaction time should be considered. The reaction temperature can be selected in the range of 25° to 80° C., still preferably 30° to 70° C., while the reaction time can be determined experimentally with the guidance of the results (yield and purity) obtained by carrying out the experiments at varied temperatures. With respect to the reaction time, the so-called minimum required time was observed. The results of the reaction did not substantially vary at temperatures within the most preferred range, as long as the reaction was carried out for a time longer than the predetermined time. This result is unexpected from the fact that the acetylation proceeded to the diacetylation stage after a short period of time and therefore salts of monoacetyl phosphate could not be obtained in the prior art described in the above West German Patent.

In the prior art using the compound represented by formula (I), wherein m is 1 (n is 2) as a raw material, the reaction mixture becomes homogeneous. On the contrary, in the present invention, the reaction proceeds in a solid-liquid coexistent state from the beginning to the end. As described above, when a salt of phosphoric acid represented by formula (I) wherein m is near 2 is used, a lithium salt of monoacetyl phosphate can be peculiarly and directly obtained in a solid form, and precipitates from the acetylation liquid. Probably, therefore, undesirable diacetylation is substantially prevented, even if the reaction time was longer. Accordingly, with respect to the reaction time, only the minimum required time must be noted. For example, at 30° C., the reaction time of 30 hours is not sufficient and a longer time is required, while the time of 20 hours is sufficient at 35° C.

In this method, the acetylation is always a heterogeneous reaction and therefore it is necessary to stir the reaction mixture in order to carry out the reaction smoothly. The excess of acetic anhydride and the acetic acid generated by the reaction act as liquid media, but it is preferred to add an inert solvent at the beginning. The kind of the inert solvents is the same as described in "phosphoric acid process". A representative example of the inert solvents is acetic acid. The amount of the inert solvent must be enough to carry out smoothly the above heterogeneous reaction under stirring.

The white crystalline reaction product can be separated, purified and analyzed according to the same method as described in "Phosphoric acid process". This product is identified as lithium salt of monoacetyl phosphate having an active phosphoric acid content of 5.2 to 5.8 mmol/g.

According to this method, a solid, lithium salt of monoacetyl phosphate can be obtained by a simple solidliquid separating method, by selecting a specified lithium salt of phosphoric acid having a molar ratio of Li to PO4 of near 2 as a substance for the acetylation with acetic anhydride. This product has also a high purity as determined by an enzymatic assay.

[Sodium or potassium phosphate process]

In this method, the acetylation is carried out in acetic acid in which the phosphate as a raw material can not be completely dissolved. Therefore this method essentially has a possibility that the acetylation may proceed to the diacetyl product forming stage, similarly to the heterogeneous acetylation according to the prior art. However the inventors of the present invention have fully examined the results of the reaction and have found that the progress of the acetylation in acetic acid medium to the diacetylation step is not uncontrollable and it is possible to quench the reaction at substantially the monoacetylation stage. The present invention has been accomplished on the basis of this finding.

This method relates to a process for the preparation of a salt of acetyl phosphate characterized in that sodium or potassium phosphate is acetylated with acetic anhydride in acetic acid and an ionic lithium compound is added to the reaction mixture of the monoacetylation stage to thereby precipitate monoacetyl phosphate in the form of a salt containing lithium, followed by separating the salt.

The salt of acetyl phosphate obtained according to this method is a composition which has one acetyl group per molecule and contains lithium ions as cation. The number of lithium atoms contained in the salt is not limited to a stoichiometric value such as 1 or 2. Further, the salt may contain sodium or potassium ion which is derived from the corresponding raw material. The present invention does not aim at obtaining a pure substance, but aims at obtaining a salt of acetyl phosphate which can act as an active raw material in the reaction involving acetate kinase. It was confirmed by the enzymatic assay that the salt of acetyl phosphate obtained according to this process has a desired reactivity.

Examples of the sodium orthophosphate to be used in this method include not only commercially available chemicals having a stoichiometric composition, such as $NaH_2PO_4$, $NaH_2PO_4.H_2O$, $NaH_2PO_4.2H_2O$, $Na_2HPO_4$, $Na_2HPO_4.2H_2O$, $Na_2HPO_4.7H_2O$, $Na_2HPO_4.12H_2O$, $Na_3PO_4$ or $Na_3PO_4.12H_2O$, but also anhydrous or hydrous sodium phosphates obtained by adding sodium acetate (anhydrous), sodium acetate (trihydrate), sodium hydroxide, sodium carbonate (anhydrous), sodium carbonate (monohydrate), sodium carbonate (decahydrate), sodium bicarbonate or the above commercially available sodium orthophosphates to a homogeneous solution of an available orthophosphoric acid, such as 100% phosphoric acid, 98% phosphoric acid (crystalline), 89% phosphoric acid, 85% phosphoric acid or 75% phosphoric acid, in acetic acid.

Examples of the potassium orthophosphate to be used in this method include not only available chemicals having a stoichiometric composition, such as $KH_2PO_4$, $K_2HPO_4$, $K_2HPO_4.3H_2O$, $K_3PO_4$ or $K_3PO_4.7H_2O$, but also anhydrous or hydrous potassium orthophosphates obtained by adding potassium acetate, potassium hydroxide, potassium carbonate (anhydrous), potassium carbonate (sesquihydrate), potassium bicarbonate or the above available potassium orthophosphates to a homogeneous solution of the above available orthophosphate in acetic acid.

Similarly to the case of a lithium salt of phosphoric acid, hereinafter formula (II) will be used to describe the composition of the sodium or potassium salt.

$$(Na, K)_m H_n PO_4 \cdot xH_2O \qquad (II)$$

wherein m, n, x and the meaning of the formula are the same as in formula (I).

The sodium or potassium orthophosphates to be used in this method are those represented by formula (II), wherein preferably
$3.0 \geq m \geq 0.5$
$2.5 \geq n \geq 0$, and
$5.0 \geq x \geq 0$,
still preferably
$3.0 \geq m \geq 0.8$,
$2.2 \geq n \geq 0$, and
$3.0 \geq x \geq 0$.

The reactivities of the sodium and potassium salts as a starting material to acetic anhydride contained in acetic acid are parallel each other, as far as other conditions are the same. Of course, salts containing both sodium and potassium can be used.

In this method, acetic anhydride serves as an acetylating agent and the acetylation is carried out in the presence of an inert solvent such as acetic acid. The amount of acetic anhydride to be used is determined mainly depending on the amount of water contained in the orthophosphate as a raw material and the kind of an ionic lithium compound to be used as a precipitating agent. Acetic anhydride also reacts with water contained in the reaction mixture to thereby form acetic acid, thus keeping the reaction mixture essentially water-free. Accordingly, when a lithium compound which contains the water of crystallization or generates water by the neutralization with acetylphosphoric acid, such as lithium hydroxide (anhydrous), lithium hydroxide (monohydrate) or lithium carbonate, is used as the ionic lithium compound, it is preferred that acetic anhydride is present in a amount enough to consume the water, thus protecting the objective product from the undesired hydrolysis. Accordingly, additional acetic anhydride may be added before the precipitation step (see, for example, Example 27). The molar ratio of acetic anhydride to orthophosphate in the acetylation is generally from 3 to 15, still preferably from 4 to 8, while the molar ratio of acetic acid to orthophosphate at the beginning of the acetylation is generally from 2 to 15, still preferably from 3 to 10. Sodium or potassium orthophosphate is used as a raw material in this method and the product is lithium salt of acetyl phosphate. Therefore, the reaction mixture contains sodium or potassium acetate. If the acetate is present in an amount exceeding its solutiblity in the precipitation step, the acetate will separate out, thus making the separation difficult. The above acetate can be dissolved in acetic acid at an ordinary temperature and therefore, if necessary, acetic acid may be added in the precipitation step (see, for example, Example 29).

With respect to the acetylation conditions, the temperature and especially the reaction time are critical in order to arrest the reaction at the monoacetylation stage. The reaction temperature can be selected in the range of 20° to 80° C., but the reaction time must be controlled strictly. Especially, if the reaction time was longer than the optimum one, a significant decrease in the yield of the product is observed (see Comparative Example). This decrease occurs because the orthophosphate is diacetylated and the resulting diacetylate does not precipitate by the addition of a lithium salt. The optimum reaction time can be easily determined by observing the progress of the reaction actually. The acetylation in this method belongs to a heterogeneous reaction, and the orthophosphate is monoacetylated in the presence of acetic acid with the gradual change of the reaction mixture into a homogeneous solution. The optimum reaction time can be determined by measuring the turbidity of the reaction mixture or by observing the residual amount of solid in the reaction mixture. The reaction time is generally varied over the range of from 5 minutes to 3 hours, depending on the reaction temperatures. Actually, when the reaction mixture becomes substantially solid-free, it is ideal for the reaction temperature to be about 30° C., still preferably about 20° C. When unreacted orthophosphate remains, it is recommended to carry out the precipitation after the filtration. It is effective in the smooth accomplishment of the reaction to pulverize the phosphate as a raw material and stir the reaction mixture, thus increasing the rate of dissolution, because the acetylation is a heterogeneous reaction.

Immediately after the solution of the monoacetylation stage has been obtained according to the above procedure, an ionic lithium compound is added to the solution to thereby precipitate monoacetyl phosphate in the form of its salt including lithium salt, followed by separation. This precipitation step is generally carried out at about 30° C., still preferably while keeping the mixture at about 20° C. by cooling. This step prevents the acetylation from proceeding to the diacetylation stage and thereby the objective product can be separated from the medium containing acetic acid. The preferred ionic lithium compound to be added immediately after the turbidity due to the phosphate which is present at the beginning of the acetylation has essentially disappeared is a lithium compound selected from among lithium acetate, lithium hydroxide (anhydrous), lithium hydroxide (monohydrate) and lithium carbonate. Lithium compounds containing an anion which is liable to cause a side reaction, such as lithium chloride, must be avoided. The ionic lithium compound may be added in the form of powder or dispersion in a medium such as acetic acid. After the addition, the reaction mixture is further stirred until a homogeneous slurry results.

In this step, lithium hydroxide (anhydrous), lithium hydroxide (monohydrate) or lithium carbonate may be pretreated with acetic anhydride or a mixture of acetic acid and acetic anhydride to form anhydrous lithium acetate, followed by using the anhydrous salt in the precipitation step. The molar ratio of lithium ion to orthophosphate as a raw material is preferably from 1.5 to 2.5, still preferably from 1.7 to 2.2.

The white crystalline solid obtained in the precipitation step can be easily separated from the reaction mixture by separation means such as filtration and the separated solid is washed with an organic solvent such as acetic acid or methanol and dried under a reduced pressure similarly to the case in "Lithium phosphate process".

It is confirmed by the enzymatic assay that the content of active phosphoric acid of this product is about 5 to 6 mmol/g.

According to this method, the monoacetylation stage can be arrested in the heterogeneous acetylation of a phosphate salt with acetic anhydride in acetic acid, by means of adding an ionic lithium compound thereby quenching the reaction and enabling facile separation of the monoacetyl phosphate salt. This has not been realized in the prior art.

PREFERRED EMBODIMENT OF THE INVENTION

The present invention will now be described in more detail by the following Examples.

Referential Examples

Analysis of a salt of acetyl phosphate by liquid chromatography

A sample of a salt of acetyl phosphate can be separated and analyzed according to the following conditions. Acetates, diacetyl phosphate and monoacetyl phosphate can be detected.

[Conditions for liquid chromatography]

Column: Nagel Nucleosil 10-$(CH_3)_2N$ 4.6 mm$\phi \times$5 cm L+4.6 mm$\phi \times$25 cm L
column temperature : 0° C. (ice-water bath)
mobile phase: 1.6 wt % aqueous solution of $NH_4H_2PO_4$ (PH 4.60)
flow veclocity: 1.5 ml/min
detector: UVIDEC-III manufactured by Nippon Bunko, 210 nm
data processor: SIC model 7000 AS

[Retention time of each component]

| Component | Retention time (min.) |
| --- | --- |
| acetate | 4.3 |
| salt of diacetyl phosphate | 4.8 |
| salt of monoacetyl phosphate | 6.7 |

[Method of analysis]

About 50 mg of a sample of a salt of acetyl phosphate is dissolved in 1 ml of distilled water precooled in an ice-water bath overnight. A 10 μl aliquot of the solution is taken up by a microsyringe and a chromatogram is recorded. The relative purity of the sample is determined by comparing the peak area of the sample with that of a standard sample (lithium potassium acetyl phosphate, a product of Boehringer Manheim GmbH). The purity of the standard sample is determined by the enzymatic assay according to the procedure described in J. Org. Chem. 40, 2516-9 (1975).by G. M. Whitesides et al. The purity is represented as the concentration of the active phosphate (hereinafter referred to as "∼P") by a unit of mmol/g.

EXAMPLE 1

183.5 g (1.80 mol) of acetic anhydride was added to a mixture of 144.7 g (2.41 mol) of acetic acid and 35.2 g (0.359 mol) of 100% phosphoric acid (prepared according to the procedure described in J. Org. Chem., 40, 2518). The mixture was stirred at 30° C. for 60 minutes. The resulting homogeneous solution was cooled to 20° C. and lithium carbonate 26.7 g (0.361 mol) was added to the solution over 7 minutes. The obtained mixture was stirred at 20° to 25° C. for 4 hours. The resulting colorless precipitate was suction-filtered by the use of a glass filter (G-2), washed with 200 ml of acetic acid and 350 ml of methanol and dried under a reduced pressure to obtain 51.1 g of lithium salt of monoacetyl phosphate as a crystalline powder. The purity of the product as determined by liquid chromatographic method described in Referential Example was ∼P=5.49 mmol/g, while that by the enzymatic assay was ∼P=5.41 mmol/g.

EXAMPLE 2

105.3 g (1.03 mol) of acetic anhydride was added dropwise to a mixture of 110.2 g (1.84 mol) of acetic acid and 40.2 g (0.410 mol) of 100% phosphoric acid under stirring at 10° C. over 60 minutes, followed by adding 29.2 g (0.395 mol) of lithium carbonate at the same temperature. The resulting slurry was stirred at 20° C. for 3 hours and then at 35° C. for 5 hours. The precipitate was suction-filtered and treated according to the same procedure as described in Example 1 to obtain 50.3 g of a salt of acetyl phosphate. The purity of the salt as determined by liquid chromatography was ∼P=5.79 mmol/g.

EXAMPLE 3

190.2 g (1.86 mol) of acetic anhydride was added to a mixture of 149.9 g (2.50 mol) of acetic acid and 36.5 g (0.372 mol) of 100% phosphoric acid and the resulting mixture was stirred at 20° C. for 60 minutes. 27.3 (0.369 mol) of lithium carbonate was added to the resulting homogeneous reaction mixture, followed by stirring at 20° C. for 3 hours. The reaction mixture was allowed to stand at that temperature overnight. The resulting precipitate was suction-filtered and treated according to the same procedure as described in Example 1 to obtain 55.6 g of a salt of acetyl phosphate. The purity of the salt as determined by liquid chromatography was ∼P=5.26 mmol/g.

EXAMPLE 4

214.4 g (2.10 mol) of acetic anhydride was added dropwise to a mixture of 40.1 g (0.348 mol) of commercial 85% phosphoric acid and 110.2 g (1.84 mol) of acetic acid at 10° C., over 40 minutes, followed by adding 27.5 (0.372 mol) of lithium carbonate at that temperature. The resulting slurry was stirred at 20° C. for 3 hours and then at 30° C. for 17 hours, and treated according to the same procedure as described in Example 1 to obtain 55.1 g of a salt of acetyl phosphate. The purity of this salt as determined by liquid chromatography was ∼P=5.70 mmol/g.

EXAMPLE 5

213.1 g (2.09 mol) of acetic anhydride was added dropwise to a mixture of 40.2 g (0.349 mol) of commercial 85% phosphoric acid and 120.4 g (2.00 mol) of acetic acid under stirring at 10° C. for 60 minutes, followed by the addition of 17.0 g (0.710 mol) of lithium hydroxide (anhydrous). The resulting slurry was stirred at about 25° C. for 3 hours and then at 35° C. for 5 hours and treated according to the same procedure as described in Example 1 to obtain 53.6 g of a salt of acetyl phosphate. The purity of this salt as determined by liquid chromatography was ∼P=5.35 mmol/g.

EXAMPLE 6

176.6 g (1.73 mol) of aceticanhydride was added dropwise to a mixture of 40.2 g (0.349 mol) of commercial 85% phosphoric acid and 164.9 g (2.75 mol) of acetic acid under stiring. The mixture was further stirred at 20° C. for 2 hours. 25.7 g (0.348 mol) of lithium carbonate was added to the resulting homogeneous reaction product. The mixture was stirred for 3 hours at that temperature, allowed to stand overnight and treated according to the same procedure as described in Example 1 to obtain 44.9 g of a salt of acetyl phosphate. The purity of this salt as determined by liquid chromatography was ∼P=4.82 mmol/g.

EXAMPLE 7

109.6 g (1.07 mol) of acetic anhydride was added dropwise to a mixture of 40.2 g (0.349 mol) of commercial 85% phosphoric acid and 140.2 g (2.33 mol) of acetic acid under stirring at 15° C. over 60 minutes, followed by adding 26.7 g (0.361 mol) of lithium carbonate at that temperature. After stirring for one hour, 33.4 g (0.327 mol) of acetic anhydride was further added. The mixture was further stirred at 35° C. for 5 hours and treated according to the same procedure as described in Example 1 to obtain 53.3 g of a salt of acetyl phosphate. The purity of this salt as determined by liquid chromatography was ∼P=5.36 mmol/g.

EXAMPLE 8

124.0 g (1.21 mol) of acetic anhydride was added dropwise to a mixture of 40.0 g (0.347 mol) of commercial 85% phosphoric acid and 66.8 g (1.11 mol) of acetic acid under stirring at 10° C. over 40 minutes, followed by adding 46.7 g (0.708 mol) of lithium acetate (anhydrous) at that temperature over 10 minutes. The mixture was further stirred for 5 hours at a temperature between 20 and 25° C and treated according to the same procedure as described in Example 1 to obtain 50.6 g of a salt of acetyl phosphate. The purity of this salt as determined by liquid chromatography was ∼P=5.31 mmol/g.

EXAMPLE 9

A mixture of 100.0 g of 100% phosphoric acid, 150.2 g of ethyl acetate and 129.5 g (1.24 times as much by mol) of acetic anhydride was kept at 0° C. for 3.0 hours to obtain an acetylation mixture. 20 g of this mixture was added to each of the following mixtures and each resulting mixture was stirred at about 20° C.

| | |
|---|---|
| (A) 10 ml of acetic acid + lithium acetate | about 2 times by mol as much as phosphoric acid |
| (B) 10 ml of acetic acid + sodium acetate | |
| (C) 10 ml of acetic acid + potassium acetate | |
| (D) 10 ml of acetic acid + magnesium acetate tetrahydrate ... about equimolar with phosphoric acid | |

The mixture containing (A) gave a crystalline precipitate. It was confirmed by HPLC that this precipitate was a salt of acetyl phosphate. Neither the mixture containing (B) nor the one containing gave precipitates and the both mixtures remained substantially transparent. The mixture containing (D) resulted in a gel as a whole

EXAMPLE 10

A mixture of 22 g of 100% phosphoric acid, 29 g of methyl acetate and 30 g of acetic anhydride was kept at 0 to 3° C. for 3.5 hours. 50 g of acetic acid was added to the reaction mixture to thereby dilute the mixture, followed by the addition of 16 g of $Li_2CO_3$. After removing a cooling bath, the reaction mixture was stirred to generate a powdery precipitate with the dissolution of $Li_2CO_3$ A part of the precipitate was filtered and analyzed by HPLC. It was confirmed that this precipitate contained a salt of acetyl phosphate.

EXAMPLE 11

The same procedure as described in Example 10 was repeated except that the following solvent systems were used instead of methyl acetate. In these cases, the precipitate of a salt of acetyl phosphate was confirmed similarly.
(i) a mixture of isopropyl ether and ethyl acetate in a ratio of 3:2
(ii) a mixture of methyl t-butyl ether and ethyl acetate in a ratio of 3:2
(iii) tetrahydrofuran
(iv) isopropyl acetate

EXAMPLE 12

25.6 g (0.346 mol) of lithium carbonate was added to a mixture of 40.0 g (0.347 mol) of commercial 85% phosphoric acid and 140 g (2.33 mol) of acetic acid. The mixture was stirred at room temperature to obtain a slurry containing a phosphate having a composition corresponding to $Li_{2.00}H_{1.00}PO_4 \cdot 1.96H_2O$. 177 g (1.73 mol) of acetic anhydride was added dropwise to the resulting homogeneous slurry. The reaction mixture was gradually heated to 35° C. and stirred at that temperature for 20 hours. The reaction mixture maintained a slurry form containing both solid and liquid from the beginning to the end. The reaction mixture was cooled to 25° C. and the solid was suction-filtered by the use of a glass filter (G2), washed with 240 g of acetic acid and 420 g of methanol and dried under a reduced pressure to obtain 47.4 g of a white crystalline powder. The content of the active phosphate in this powder as determined by the enzymatic assay was 5.53 mmol/g. The purity of the salt of monoacetyl phosphate as determined by liquid chromatography was 5.58 mmol/g.

EXAMPLE 13

25.5 g (0.346 mol) of lithium carbonate was added to a mixture of 40.0 g (0.347 mol) of commercial 85% phosphoric acid and 140 g (2.33 mol) of acetic acid. The mixture was stirred at a room temperature to obtain a slurry containing a phosphate having a composition corresponding to $Li_{2.00}H_{1.00}PO_4 \cdot 1.96H_2O$. 248 g (2.43 mol) of acetic anhydride was added dropwise to the resulting homogeneous slurry. The reaction mixture was gradually heated to 35° C., stirred at that temperature for 29 hours, cooled to 20° C. and treated according to the same procedure as described in Example 12 to obtain 53.7 g of a salt of acetyl phosphate. The purity of the salt as determined by liquid chromatography was $\sim P = 5.69$ mmol/g.

EXAMPLE 14

25.6 g (0.346 mol) of lithium carbonate was added to a mixture of 40.0 g (0.347 mol) of commercial 85% phosphoric acid and 100 g (1.67 mol) of acetic acid. The mixture was stirred at a room temperature to obtain a slurry containing a phosphate having a composition corresponding to $Li_{2.00}H_{1.00}PO_4 \cdot 1.96H_2O$. 177 g (1.73 mol) of acetic anhydride was added dropwise to the resulting homogeneous slurry. The mixture was stirred at 35° C. for 48 hours and treated according to the same procedure as described in Example 12 to obtain 53.0 g of a salt of acetyl phosphate. The purity of the salt as determined by liquid chromatography was $\sim P = 5.61$ mmol/g.

EXAMPLE 15

27.5 g (0.655 mol) of lithium hydroxide (monohydrate) was added to a mixture of 37.0 g (0.321 mol) of commercial 85% phosphoric acid and 115 g (1.92 mol) of acetic acid. The mixture was stirred at 35° C. until a homogeneous slurry was formed, to thereby obtain a mixture containing a phosphate of a composition corresponding to $Li_{2.04}H_{0.96}PO_4 \cdot 5.04H_2O$. 265 g (2.60 mol) of acetic anhydride was added dropwise to the resulting mixture. The mixture was carefully heated to 60° C., stirred for 6.5 hours and treated according to the same procedure as described in Example 12 to obtain 51.1 g of a salt of acetyl phosphate. The purity of the salt as determined by liquid chromatography was $\sim P = 5.43$ mmol/g.

EXAMPLE 16

23.7 g (0.321 mol) of lithium carbonate was added to a mixture of 37.0 g (0.321 mol) of commercial 85% phosphoric acid and 115 g (1.92 mol) of acetic acid. The mixture was stirred at room temperature to obtain a slurry containing a phosphate of a composition corresponding to $Li_{2.00}H_{1.00}PO_4 \cdot 1.96H_2O$. 265 g (2.60 mol) of acetic anhydride was added dropwise to the resulting homogeneous slurry. The mixture was carefully heated to 70° C., stirred for 8 hours and treated according to the same procedure as described in Example 12 to obtain 46.8 g of a salt of acetyl phosphate. The purity of this salt as determined by liquid chromatography was $\sim P = 5.20$ mmol/g.

EXAMPLE 17

26.0 g (0.352 mol) of lithium carbonate was added to a mixture of 34.0 g (0.347 mol) of 100% phosphoric acid prepared by adding phosphorus pentaoxide to commercial 85% phosphoric acid and 80.0 g (1.33 mol) of acetic acid. The mixture was stirred at room temperature to obtain a slurry containing a phosphate of a composition corresponding to $Li_{2.03}H_{0.97}PO_4 \cdot 1.01H_2O$. 100 g (0.980 mol) of acetic anhydride was added dropwise to the resulting homogeneous slurry. The mixture was stirred at 45° C. for 20 hours and treated according to the same procedure as described in Example 12 to obtain 52.0 g of a salt of acetyl phosphate. The purity of this salt as determined by liquid chromatography was $\sim P = 5.56$ mmol/g.

EXAMPLE 18

16.5 g (0.689 mol) of lithium hydroxide (anhydrous) was added to a mixture of 40.0 g (0.347 mol) of commercial 85% phosphoric acid and 100 g (1.67 mol) of acetic acid. The mixture was stirred at 35° C. for one day to obtain a mixture containing a phosphate of a composition corresponding to $Li_{1.99}H_{1.01}PO_4 \cdot 2.95H_2O$. 177 g (1.73 mol) of acetic anhydride was added dropwise to the resulting mixture. The mixture was carefully heated to 45° C., stirred for 22 hours and treated according to the same procedure as described in Example 12 to obtain 46.1 g of a salt of acetyl phosphate. The purity of this salt as determined by liquid chromatography was $\sim P = 5.77$ mmol/g.

EXAMPLE 19

25.9 g (0.351 mol) of lithium carbonate was added to a mixture of 40.0 g (0.347 mol) of commercial 85% phosphoric acid and 80.0 g (1.33 mol) of acetic acid. The mixture was stirred at room temperature for one hour to obtain a mixture containing a phosphate of a composition corresponding to $Li_{2.02}H_{0.98}PO_4 \cdot 1.97H_2O$. 350 g (3.43 mol) of acetic anhydride was added dropwise to the resulting mixture. The mixture was stirred at 35° C. for 43 hours and treated according to the same procedure as described in Example 12 to obtain 48.5 g of a salt of acetyl phosphate. The purity of this salt as determined by liquid chromatography was $\sim P = 5.36$ mmol/g.

EXAMPLE 20

26.9 g (0.364 mol) of lithium carbonate was added to a mixture of 40.0 g (0.347 mol) of commercial 85% phosphoric acid and 140 g (2.33 mol) of acetic acid. The mixture was stirred at a room temperature to obtain a mixture containing a phosphate of a composition corresponding to $Li_{2.10}H_{0.90}PO_4 \cdot 2.01H_2O$. 177 g (1.73 mol) of acetic anhydride was added dropwise to the resulting homogeneous mixture. The mixture was stirred at 45° C. for 20 hours and treated according to the same procedure as described in Example 12 to obtain 57.7 g of a salt of acetyl phosphate. The purity of this salt as determined by liquid chromatography was $\sim P = 5.30$ mmol/g.

EXAMPLE 21

The same procedure as described in Example 20 was repeated except that 24.3 g (0.329 mol) of lithium carbonate was used, to obtain a mixture containing a phosphate of a composition corresponding to $Li_{1.90}H_{1.10}PO_4 \cdot 1.91H_2O$. Then, the reaction was carried out as described in Example 20 to obtain 40.8 g of a salt of acetyl phosphate. The purity of this salt as determined by liquid chromatography was $\sim P = 5.49$ mmol/g.

EXAMPLE 22

147 g (1.39 mol) of sodium carbonate was added to a mixture of 260 g (2.26 mol) of commercial 85% phosphoric acid and 957 g (15.9 mol) of acetic acid under stirring and cooling. The orthophosphate as a raw material had a composition corresponding to $Na_{1.2}H_{1.8}PO_4 \cdot 1.6H_2O$. After evolution of a gas had ceased (after about one hour), 1,470 g (14.4 mol) of acetic anhydride was added dropwise to the resulting reaction mixture. The mixture was carefully heated to 57° C. over 40 minutes and kept at that temperature for 5 minutes. The reaction temperature was lowered to 20° C. over 30 minutes by the use of a water both. The reaction mixture became clear after about 50 minutes since the beginning of the reaction. 158 g (2.14 mol) of lithium carbonate was added to the mixture over about 40 minutes and the mixture was stirred at room temperature for 5 hours. The resulting precipitate was filtered with suction by the use of a glass filter (G2), washed with acetic acid (700 ml) and methanol (1200 ml) and dried under a reduced pressure to obtain 293 g of lithium salt of acetyl phosphate as a mobile powder. The purity of this salt as determined by the method described in Referential Example was $\sim P = 6.15$ mmol/g, while that determined by the enzymatic essay was 6.01 mmol/g.

COMPARATIVE EXAMPLE

According to the procedure described in Example 3 of West German Pat. No. 2831831, a mixture of 13.8 g (0.1 mol) of $NaH_2PO_4 \cdot H_2O$, 48 g (0.8 mol) of acetic acid and 82 g (0.8 mol) of acetic anhydride was stirred in a nitrogen atmosphere for 5 hours, while keeping the mixture at 45° to 60° C. by heating. The resulting colorless, clear solution was cooled to 25° C., and 7.4 g (0.1 mol) of lithium carbonate was added to the solution, followed by stirring at that temperature. The reaction mixture became slightly turbid but did not form any precipitate separable by filtration even after 5 days.

EXAMPLE 23

100 g (1.2 mol) of sodium bicarbonate was added to a mixture of 175 g (1.5 mol) of commercial 85% phosphoric acid and 500 g (8.3 mol) of acetic acid under stirring and cooling. The resulting orthophosphate as a raw material had a composition coresponding to $Na_{0.8}H_{2.2}PO_4 \cdot 1.7H_2O$. 857 g (8.6 mol) of acetic anhydride was added dropwise to the reaction mixture. Immediately after the obtained reaction mixture had been carefully heated to 63° C., it was cooled in an ice-water bath. After 23 minutes since the beginning of the reaction, the reaction mixture became clear. 113 g (1.5 mol) of lithium carbonate was added to the reaction mixture cooled to 20° C. over 25 minutes. The mixture was stirred at room temperature for 7 hours and treated according to the same procedure as described in Example 22 to obtain 237 g of lithium salt of acetyl phosphate. The purity was determined by liquid chromatography was $\sim P = 5.3$ mmol/g.

EXAMPLE 24

14 g (0.33 mol) of sodium hydroxide of a purity of 95% was added to a mixture of 37 g (0.32 mol) of commercial 85% phosphoric acid and 115 g (1.9 mol) of acetic acid under stirring and cooling and the obtained mixture was stirred until a homogeneous slurry was formed. The orthophosphate as a raw material had a composition corresponding to $NaH_2PO_4 \cdot 2.1H_2O$. 265 g (2.6 mol) of acetic anhydride was added to the reaction mixture. The obtained mixture was kept at 60° C. for 40 minutes by heating and then cooled to 20° C. 24 g (0.325 mol) of lithium carbonate was added to the resulting clear reaction solution over about 10 minutes. The mixture was stirred at room temperature for 5 hours and treated according to the same procedure as described in example 22 to obtain 55 g of lithium salt of acetyl phosphate. The purity as determined by liquid chromatography was $\sim P=5.0$ mmol/g.

EXAMPLE 25

130 g (1.3 mol) of potassium bicarbonate was added to a mixture of 150 g (1.3 mol) of commercial 85% phosphoric acid and 450 g (7.5 mol) of acetic acid under stirring and cooling. The orthophosphate as a raw material had a composition corresponding to $KH_2PO_4 \cdot 2.0H_2O$. 800 g (7.8 mol) of acetic anhydride was added to the mixture. The reaction mixture was kept at 65° C. for 75 minutes by heating and rapidly cooled to 20° C. 166 g (2.5 mol) of lithium acetate (anhydrous) was added to the resulting clear reaction solution over about 70 minutes. The mixture was stirred at a room temperature for 5 hours and treated according to the same procedure as described in Example 22 to obtain 187 g of lithium salt of acetyl phosphate. The purity as determined by liquid chromatography was $\sim P=5.4$ mmol/g.

EXAMPLE 26

131 g (1.24 mol) of sodium carbonate was added to a mixture of 260 g (2.26 mol) of commercial 85% phosphoric acid and 61 g (3.39 mol) of water under stirring and cooling. The orthophosphate as a raw material had a composition corresponding to $Na_{1.1}H_{1.9}PO_4 \cdot 3.0H_2O$. 1,610 g (15.8 mol) of acetic anhydride was added to the reaction mixture. The reaction mixture was carefully heated to 55° C. over 70 minutes and gradually cooled to 25° C. over 40 minutes. The reaction mixture became clear after about 80 minutes since the beginning of the reaction. 158 g (2.14 mol) of lithium carbonate was added to the resulting clear solution. The mixture was stirred at room temperature for 4 hours and treated according to the same procedure as described in Example 22 to obtain 300 g of lithium salt of acetyl phosphate. The purity as determined by liquid chromatography was $\sim P=5.7$ mmol/g.

EXAMPLE 27

118 g (1.20 mol) of potassium acetate (anhydrous) was added to a mixture of 140 g (1.22 mol) of commercial 85% phosphoric acid and 250 g (4.16 mol) of acetic acid under stirring and cooling. The orthophosphate as a raw material had a composition corresponding to $KH_2PO_4 \cdot 0.96H_2O$. 400 g (3.92 mol) of acetic anhydride was added to the reaction mixture. The mixture was heated to 75° C. over 25 minutes, kept at that temperature for 25 minutes and cooled rapidly to 20° C. 500 g (4.9 mol) of acetic anhydride was added dropwise to the resulting clear liquid, followed by the addition of 107 g (2.55 mol) of lithium hydroxide (monohydrate). The mixture was stirred at about 30° C. for 7 hours and treated according to the same procedure as described in Example 22 to obtain 125 g of lithium salt of acetyl phosphate. The purity as determined by liquid chromatography was $\sim P=5.5$ mmol/g.

EXAMPLE 28

A mixture of 178 g (1.0 mol) of commercial $Na_2HPO_4 \cdot 2H_2O$, 474 g (7.9 mol) of acetic acid and 504 g (4.9 mol) of acetic anhydride was stirred at 20 to 26° C. for 80 minutes. 70 g (0.95 mol) of lithium carbonate was added to the resulting colorless, clear solution. The mixture was further stirred at room temperature for 4 hours. The resulting precipitate was filtered, washed with acetic acid and methanol and dried under a reduced pressure to obtain 140 g of lithium salt of acetyl phosphate. The purity as determined by liquid chromatography was $\sim P=5.0$ mmol/g.

EXAMPLE 29

100 g (0.47 mol) of commercial $K_3PO_4$ (anhydrous) was added to a mixture of 340 g (5.7 mol) of acetic acid and 17 g (0.94 mol) of water. The resulting mixture was stirred at room temperature overnight. 242 g (2.4 mol) of acetic anhydride was added to the mixture. The reaction mixture was heated to 60° C. over about 40 minutes, kept at that temperature for 25 minutes and rapidly cooled in an ice-water bath. 83 g (0.8 mol) of acetic anhydride was added to the resulting colorless clear solution at about 22° C., followed by the addition of 36.5 g (0.49 mol) of lithium carbonate and 128 g (2.1 mol) of acetic acid. The mixture was stirred at room temperature for 3 hours. The resulting precipitate was treated according to the same procedure as described in Example 28 to obtain 61 g of lithium salt of acetyl phosphate. The purity as determined by liquid chromatography was $\sim P=5.5$ mmol/g.

EXAMPLE 30

A mixture of 41 g (0.3 mol) of commercial $NaH_2PO_4 \cdot H_2O$, 143 g (2.4 mol) of acetic acid and 245 g (2.4 mol) of acetic anhydride was stirred at 60° C. for 70 minutes. The resulting colorless, clear solution was rapidly cooled to 20° C. 43 g (0.65 mol) of lithium acetate (anhydrous) was added to the solution. The resulting precipitate was treated according to the same procedure as described in example 28 to obtain 41 g of lithium salt of acetyl phosphate. The purity as determined by liquid chromatography was $\sim P=5.0$ mmol/g.

EXAMPLE 31

A mixture of 50 g (0.32 mol) of commercial $NaH_2PO_4 \cdot 2H_2O$, 200 g (3.3 mol) of acetic acid and 165 g (1.6 mol) of acetic anhydride was stirred at 60° C. for 40 minutes. The resulting colorless, clear solution was rapidly cooled to 20° C. 42 g (0.64 mol) of lithium acetate (anhydrous) was added to the solution. The resulting precipitate was treated according to the same procedure as described in Example 28 to obtain 43 g of lithium salt of acetyl phosphate. The purity as determined by liquid chromatography was $\sim P=5.2$ mmol/g.

EXAMPLE 32

A mixture of 56 g (0.32 mol) of commercial $K_2HPO_4$ (anhydrous), 200 g (3.3 mol) of acetic acid and 98 g (0.96 mol) of acetic anhydride was stirred at 80° C. for 30 minutes. The resulting colorless, clear solution was rapidly cooled to 25° C. 24 g (0.32 mol) of lithium carbonate and 60 g (1.0 mol) of acetic acid were added successively. The mixture was further stirred at room temperature overnight. The resulting precipitate was treated according to the same procedure as described in Example 28 to obtain 27 g of lithium salt of acetyl phosphate. The purity as determined by liquid chromatography was ~P=5.4 mmol/g.

What we claim:

1. A process for preparing a solid lithium monoacetyl phosphate salt, comprising the steps of: in a reaction system, acetylating (1) a phosphate material having the composition $$Li_mH_nPO_4 \cdot xH_2O.$$

wherein
$2.2 \geq m \geq 1.5$
$1.5 \geq n \geq 0.8$, and
$6.0 \geq x \geq 0$,
with (2) acetic anhydride, in the presence of acetic acid as an inert solvent, whereby to form a precipitate of said lithium monoacetyl phosphate salt in said reaction system; and then recovering said lithium monoacetyl phosphate salt from the reaction system.

2. The process as set forth in claim 1, wherein m is from 1.9 to 2.1 and n is from 1.1 to 0.9.

3. The process as set forth in claim 1, wherein the effective molar ratio of acetic anhydride to the phohsphate material is from about 1.5 to 10.

4. The process as set forth in claim 1, wherein the effective molar ratio of acetic anhydride to the phosphate material is from about 2.0 to 8.0.

5. The process as set forth in claim 1, wherein the acetylation is conducted at a temperature within the range of from about 25° to 80° C.

6. The process as set forth in claim 1, wherein the acetylation is conducted at a temperature within the range of from about 30° to 70° C.

7. The process as set forth in claim 1 in which, in the reaction system, the molar ratio of acetic acid to said phosphate material is from 2 to 15.

8. A process for preparing a solid lithium monoacetyl phosphate salt, consisting essentially of the steps of: in a reaction system, adding acetic anhydride to a reaction solution of phosphoric acid dissolved in acetic acid as in inert solvent, and acetylating said phosphoric acid at a temperature of from about 10° to about 30° C. to form a monoacetyl phosphate in said reaction solution; then adding a compound effective for supplying lithium ions to said reaction solution so that the molar ratio of lithium ion to phosphate radical in said reaction solution is from 1.5 to 2.3, stirring said reaction solution to mix said compound therein to form a homogenous slurry and continuing the stirring until a precipitate of solid lithium monoacetyl phosphate salt is formed in said reaction solution, and then recovering said precipitate from said reaction solution.

9. The process of claim 8 in which the molar ratio of acetic acid to phosphoric acid is from 2 to 15, the molar ratio of acetic anhydride to phosphoric acid is from 1.5 to 10 and said compound is selected from the group consisting of lithium acetate, lithium hydroxide and lithium carbonate.

10. A process for preparing a solid lithium monoacetyl phosphate salt, consisting essentially of the steps of: in a reaction system, mixing a solution of phosphoric acid dissolved in acetic acid with a compound supplying lithium ions to obtain a slurry of said acetic acid containing phosphate material having the composition $$Li_mH_nPO_4 \cdot xH_2O.$$

wherein
$2.2 \geq m \geq 1.5$
$1.5 \geq n \geq 0.8$ and
$6.0 \geq x \geq 0$,
adding acetic anhydride to said slurry and maintaining said slurry at from 25° to 80° C. while stirring said slurry and thereby acetylating said phosphate material until a solid lithium monoacetyl phosphate salt is formed in said slurry, and then recovering said solid lithium monoacetyl phosphate salt from the slurry system.

11. The process of claim 10 in which the molar ratio of acetic acid to said phosphate material is from 2 to 15, the molar ratio of acetic anhydride to said phosphate material is 1.5 to 10 and said compound is selected from the group consisting of lithium acetate, lithium hydroxide and lithium carbonate.

12. A process for preparing a solid lithium monoacetyl phosphate salt, consistng essentially of the steps of: in a reaction system, mixing a phosphate material having the composition.

$$(Na,K)_mH_nPO_4 \cdot xH_2O$$

wherein
$3.0 \geq m \geq 0.5$
$2.5 \geq n \geq 0$
$5.0 \geq n \geq 0$
with acetic acid to form a slurry, adding acetic anhydride to said slurry and maintaining said slurry at from 20° to 80° C. while stirring said slurry and therby acetylating said phosphate material until a monoacetyl phosphate is formed; then adding to said slurry a compound effective for supplying lithium ions so that the molar ratio of lithium ion to phosphate radical in said slurry is from 1.5 to 2.5, stirring said slurry to mix said compound therein and continuing the stirring until a precipitate of solid lithium-containing monoacetyl phosphate is formed, and then recovering said precipitate from the reaction system.

13. The process of claim 12 in which the molar ratio of acetic acid to said phosphate material is from 2 to 15, the molar ratio of acetic anhydride to said phosphate material is 3 to 15 and said compound is selected from the group consisting of lithium acetate, lithium hydroxide and lithium carbonate.

* * * * *

UNITED STATES PATENT AND TRADEMARK OFFICE
CERTIFICATE OF CORRECTION

PATENT NO. : 4 753 757
DATED : June 28, 1988
INVENTOR(S) : Yoichiro UEDA et al

It is certified that error appears in the above-identified patent and that said Letters Patent is hereby corrected as shown below:

On the title page at [75] and [19] change the surname of the first inventor to ---Ueda---.

Column 19, lines 25 and 26; change "phohsphate" to ---phosphate---.

Column 20, line 38; change "$5.0 \geq n \geq 0$" to ---$5.0 \geq x \geq 0$---.

Column 20, line 41; change "therby" to ---thereby---.

Signed and Sealed this

Eighth Day of November, 1988

Attest:

DONALD J. QUIGG

Attesting Officer

Commissioner of Patents and Trademarks